United States Patent
Amiji et al.

(10) Patent No.: US 9,623,124 B2
(45) Date of Patent: Apr. 18, 2017

(54) MULTIMODAL DIAGNOSTIC TECHNOLOGY FOR EARLY STAGE CANCER LESIONS

(75) Inventors: Mansoor M. Amiji, Attleboro, MA (US); Srinivas Ganta, Boston, MA (US); Pei-Chin Tsai, Boston, MA (US)

(73) Assignee: Northeastern University, Boston, MA (US)

( * ) Notice: Subject to any disclaimer, the term of this patent is extended or adjusted under 35 U.S.C. 154(b) by 1030 days.

(21) Appl. No.: 13/636,877

(22) PCT Filed: Mar. 24, 2011

(86) PCT No.: PCT/US2011/029777
§ 371 (c)(1),
(2), (4) Date: May 8, 2013

(87) PCT Pub. No.: WO2011/119822
PCT Pub. Date: Sep. 29, 2011

(65) Prior Publication Data
US 2013/0224120 A1    Aug. 29, 2013

Related U.S. Application Data

(60) Provisional application No. 61/317,123, filed on Mar. 24, 2010.

(51) Int. Cl.
| | | |
|---|---|---|
| A61K 49/00 | (2006.01) |
| A61B 5/00 | (2006.01) |
| G01N 33/58 | (2006.01) |
| G01N 33/543 | (2006.01) |

(52) U.S. Cl.
CPC ...... *A61K 49/0091* (2013.01); *A61K 49/0032* (2013.01); *A61K 49/0056* (2013.01); *A61K 49/0058* (2013.01); *A61K 49/0065* (2013.01); *G01N 33/54346* (2013.01); *G01N 33/587* (2013.01); *A61B 5/0066* (2013.01)

(58) Field of Classification Search
None
See application file for complete search history.

(56) References Cited

U.S. PATENT DOCUMENTS

| 5,879,713 A * | 3/1999 | Roth ............. A61K 9/0024 424/423 |
| 7,022,336 B2 | 4/2006 | Papahadjopoulos et al. |
| 2008/0032920 A1 | 2/2008 | Prestwich et al. |
| 2008/0248038 A1 | 10/2008 | Corvinus et al. |
| 2010/0028453 A1 | 2/2010 | Yoo et al. |
| 2010/0068286 A1 | 3/2010 | Troiano et al. |

FOREIGN PATENT DOCUMENTS

WO    WO 2008002101 A1 *  1/2008  ........... A61K 9/5153

OTHER PUBLICATIONS

Westcott et al. Formation and adsorption of clusters of gold nanoparticles onto functionalized silica nanoparticle surfaces. 1998 Langmuir 14: 5396-5401.*
Sokolov et al. Real-time vital optical imaging of precancer using anti-epidermal growth factor receptor antibodies conjugated to gold nanoparticles. 2003 Cancer Res. 63: 1999-2004.*
Lin et al. Comparison of chitosan and gelatin coated microparticles: prepared by hot-melt method. 2003 J. Microencapsul. 20: 169-177.*
Tseng et al. Targeting efficiency and biodistribution of biotinylated-EGF-conjugated gelatin nanoparticles administered via aerosol delivery in nude mice with lung cancer. 2008 Biomaterials 29: 3014-3022.*
Balmayor, et al., "Synthesis and Functionalization of Superparamagnetic poly-ϵ-caprolactone microparticles for the selective isolation of subpopulations of Human Adipose-derived Stem Cells", J. R. Soc. Interface, vol. 8, pp. 896-908 (2011).
Bumgarner, et al., "Surface Engineering of Microparticles by Novel Protein Transfer for Targeted Antigen/Drug Delivery", J. Control Release, vol. 137 (2), pp. 90-97 (2009).
Extended European Search Report issued by the European Patent Office in corresponding European Patent Application No. EP11760209.4 dated Jul. 31, 2013 (10 pgs.).
Gardea-Torresdey, et al., "Gold Nanoparticles Obtained by Bio-Precipitation from Gold (III) Solutions", Journal of Nanoparticle Research, vol. 1 (3), pp. 397-404 (1999).
Gindy, M.E., et al., "Functional Block Copolymer Nanoparticles for Targeted Drug Delivery and Imaging", PMSE Preprints, vol. 95, pp. 989-990 (2006).
Horton, et al., "Arg-Gly-Asp (RGD) Peptides and the Anti-Vitronectin Receptor Antibody 23C6 Inhibit Dentine Resorption and Cell Spreading by Osteoclasts", Experimental Cell Reasearch, vol. 195, pp. 368-375 (1991).
International Search Report and Written Opinion issued by the U.S. Patent and Trademark Office as International Searching Authority for International Application No. PCT/US2011/029777 mailed May 27, 2011 (9 pgs.).
Kaushik, et al., "Chitosan-iron Oxide Nanobiocomposite Based Immunosensor for Ochratoxin-A", Electrochemistry Communications, vol. 10, pp. 1364-1368 (2008).
Kim, et al., "Activity-Based Assay of Matrix Metalloproteinase on Nonbiofouling Surfaces Using Time-of-flight Secondary Ion Mass Spectrometry", Anal. Chem., vol. 80, pp. 5094-5102 (2008).

(Continued)

*Primary Examiner* — Michael G. Hartley
*Assistant Examiner* — Jennifer Lamberski
(74) *Attorney, Agent, or Firm* — Posternak Blankstein & Lund LLP

(57) ABSTRACT

Disclosed herein are compositions of a multimodal detection agent and methods of fabricating the same. The multimodal detection agent comprises a plurality of metallic nanoparticles attached to a surface of a polymeric carrier. The detection agent further comprising one or more target-specific binding agents attached to the metallic nanoparticles or the polymeric carrier.

21 Claims, 4 Drawing Sheets

(56) References Cited

OTHER PUBLICATIONS

Lue, et al., "Preliminary Evaluation of a Nanotechnology-based Approach for the more Effective Diagnosis of Colon Cancers," Nanomedicine, vol. 5 (9), pp. 1467-1479 (2010).

Luna Martinez, et al., "Iron Oxide Nanoparticles Obtained from a Fe(II)—Chitosan Polymer Film", Mater. Sci. Forum: Adv. Elec. Microscop. Nanomat., vol. 644, pp. 51-55 (2010).

Mathiowitz, et al., "Biologically Erodable Microspheres as Potential Oral Drug Delivery Systems", Nature, vol. 386 (6623), pp. 410-414 (1997).

McFarland, et al., "Color My NanoWorld", J. Chem. Educ., vol. 81 (4); p. 544A-544B (2004).

Mosqueira, et al., "Poly(D, L-lactide) Nanocapsules Prepared by a Solvent Displacement Process: Influence of the Composition on Physicochemical and Structural Properties", Journal of Pharm. Sci. vol. 89 (5), pp. 614-626 (2000).

Oster, et al., "DNA Nano-Carriers from Biodegradable Cationic Branched Polyesters are Formed by a Modified Solvent Displacement Method", Journal of Controlled Release, vol. 111 (3), pp. 371-381 (2006).

Panyam, et al., "Fluorescence and Electron Microscopy Probes for Cellular and tissue Uptake of Poly(D,L-latcide-co-glycolide) Nanoparticles", International J. of Phamaceutics, vol. 262, pp. 1-11 (2003).

Papisov, M.I., et al., "Semisynthetic Hydrophilic Polyals", Biomacromolecules, vol. 6, pp. 2659-2670 (2005).

Ribeiro, et al., "Preparation of Nanodispersions Containing Beta-Carotene by Solvent Displacement Method", Food Hydrocolloids, vol. 22 (1), pp. 12-17 (2008).

Rosca, et al., "Microparticle Formation and its Mechanism in Single and Double Emulsion Solvent Evaporation", Journal of Controlled Release, vol. 99 (2), pp. 271-280 (2004).

Sainsbury, et al. "Self-Assembly of Gold Nanoparticles at the Surface of Amine- and Thiol-Functionalized Boron Nitride Nanotubes", J. Phys. Chem. C. vol. 111, pp. 12992-12999 (2007).

Sy, et al., Surface Functionalization of Polyketal Microparticles with Nitrilotriacetic Acid-Nickel Complexes for Efficient Protein Capture and Delivery, Biomaterials, vol. 31 (18), pp. 4987-4994 (2010).

Townsend, S.A., et al., "Tetanus Toxin C Fragment Conjugated nanoparticles for Targeted Drug Delivery to Neurons", Biomaterials, vol. 28 (34), pp. 5176-5184 (2007).

Tsung, et al., "Preparation and Characterization of Gelatin Surface Modified PLGA Microspheres", AAPS PharmSci., vol. 3 (1), Article 11, pp. 1-11 (2001).

Weiss, et al., "Coupling of Biotin-(poly(ethylene glycol))amine to poly(D,L-lactide-co-glycolide) Nanoparticles for Versatile Surface Modification", Bioconjugate Chemistry, vol. 18 (4), pp. 1087-1094 (2007).

Zhou, et al., "A Novel Ultraviolet Irradiation Technique for Shape-Controlled Synthesis of Gold Nanoparticles at Room Temperature", Chem. Mater., vol. 11 (9), pp. 2310-2312 (1999).

\* cited by examiner

MULTIMODAL DIAGNOSTIC TECHNOLOGY FOR EARLY STAGE CANCER LESIONS

This application is a U.S. National Phase Application under 35 U.S.C. 371 of International Patent Application No. PCT/US2011/29777 filed Mar. 24, 2011, and published as WO 2011/119822 on Sep. 29, 2011, which claims the benefit of and priority to U.S. Provisional Application Ser. No. 61/317,123, filed Mar. 24, 2010, the entire contents of which are incorporated herein by reference.

FIELD OF THE INVENTION

This invention is in the field of medicine. More specifically, this invention relates to cancer therapies utilizing microparticles and fluorescence guided scattering technology.

BACKGROUND

More than 1.5 million new cases of cancer are diagnosed per year and the mortality rates for some types of cancer remain very high. The diagnosis of tumor lesions at its inception and early intervention with surgery, radiation, and chemotherapy usually has a positive impact in the outcome of the disease.

Current oral cancer diagnosis is based on tissue transformation in advanced stage of the disease, which is confirmed by biopsy and pathological analysis. Early diagnosis technology specifically for pre-cancerous lesions that can be used in routine dental examination would provide favorably affect clinical outcome. Similarly, current colon cancer screening tests, such as colonoscopy, CT, etc., can only detect cancers that are already in advanced stages. At this stage patients already develop symptoms, such as changing in bowel habits, bloody stools, and abdominal pain. Since early stage diagnosis and intervention often leads to a total cure of the disease, there is a real need for a better diagnosis method.

SUMMARY

This disclosure relates to multimodal technology for detection of cancerous lesions. The compositions disclosed herein include multimodal detection agents comprising a plurality of metallic nanoparticles attached to a surface of a polymeric carrier. The detection agents further comprise one or more target-specific binding agents attached to the metallic nanoparticles or the polymeric carrier. In this technology, the target-specific binding agent (i.e., targeting ligand) helps in binding of microparticles specifically to cells or tissues of interest. Imaging technologies, such as OCT, are used to detect tissue morphology.

Aspects of the compositions disclosed herein include a multimodal detection agent. The detection agent comprises a plurality of metallic nanoparticles attached to a surface of a polymeric carrier. The detection agent further comprises one or more target-specific binding agents attached to the metallic nanoparticles or the polymeric carrier.

In certain embodiments, the metallic nanoparticle comprises one or more of the metals and metal oxides selected from the group consisting of gold, silver, cobalt, manganese, and iron. In particular embodiments, the metallic nanoparticle comprises gold.

In some embodiments, the polymeric carrier comprises poly(epsilon-caprolactone) and in other embodiments, the polymeric carrier comprises poly(d,l-lactide-co-glycolide). In some embodiments, the one or more target-specific binding agents is an antibody, Fab fragment, or binding fragment thereof. In particular embodiments, the one or more target-specific binding agents is an EGFR-specific antibody. In more particular embodiments, the one or more target-specific binding agents is a peptide sequence that specifically targets cell surface receptors. In even more particular embodiments, the one or more target-specific binding agents is a peptide sequence that specifically targets EGFR. In other embodiments, the one or more target-specific binding agents is an arginine-glycine-aspartate tripeptide. In still other embodiments, the one or more target-specific binding agents binds to alpha-V-beta III integrin receptor.

In certain embodiments, the polymeric carrier comprises modified poly(epsilon-caprolactone). In some embodiments, the polymeric carrier comprises at least one layer of gelatin having exposed thiol groups. In other embodiments, the metallic nanoparticles comprise gold.

In particular aspects, the metallic nanoparticles are about 2 nanometers to about 30 nanometers. In certain embodiments, the polymeric carrier is about 500 nanometers to about 10 microns.

In other embodiments, the target-specific binding agent is selected from the group consisting of antibody and peptide sequences. In more embodiments, the polymeric carrier encapsulates an imaging agent. In still more embodiments, the imaging agent is selected from the group consisting of fluorophores, radiolabels, X-ray contrast, and positron emission tomography agents. In further embodiments, the imaging agent is a near-infrared fluorescence dye. In still further embodiments, the metallic nanoparticles are about 10 to about 20 nm. In very particular embodiments, the polymeric carrier is about 1.5 microns.

In certain embodiments, the target-specific binding agent is attached to the metallic nanoparticle. In specific embodiments, the target-specific binding agent is attached to the metallic nanoparticle and the polymeric carrier.

Aspects disclosed herein include methods of manufacturing a multimodal imaging agent. The method comprises fabricating a polymeric core particle and adding at least one coating to the polymeric core particle to form a polymeric carrier. In additional aspects, the methods include attaching one or more metallic nanoparticles to the coating and functionalizing the at least one coating or one or more metallic nanoparticles with a target-specific binding agent.

In certain embodiments, the polymeric core particle comprises poly(epsilon-caprolactone). In other embodiments, the one or more metallic nanoparticles comprises one or more of the metals and metal oxides selected from the group consisting of gold, silver, and iron. In particular embodiments, the metallic nanoparticles comprise gold.

In some embodiments, the metallic nanoparticles are about 2 nanometers to about 30 nanometers. In particular embodiments, the polymeric carrier is about 500 nanometers to about 10 microns.

In certain embodiments, the target-specific binding agent is an EGFR-specific antibody. In more certain embodiments, the target-specific binding agent is an arginine-glycine-aspartate tripeptide. In still more certain embodiments, the target-specific binding agent binds to alpha-V-beta III integrin receptor.

In particular embodiments, the polymeric carrier is about 1.5 microns.

In other embodiments, fabricating a polymeric core particle further comprises encapsulating an imaging agent within the polymeric core particle. In further embodiments, the imaging agent is selected from the group consisting of fluorophores, radiolabels, and positron emission tomography agents.

In particular embodiments, the at least one coating is a thiol-modified gelatin. In further embodiments, the metallic nanoparticles are about 10 to about 20 nm. In other embodiments, the target-specific binding agent is an antibody, Fab fragment, or binding fragment thereof.

BRIEF DESCRIPTION OF THE FIGURES

The following figures are presented for the purpose of illustration only, and are not intended to be limiting.

DETAILED DESCRIPTION

1. Compositions

Figure 1:
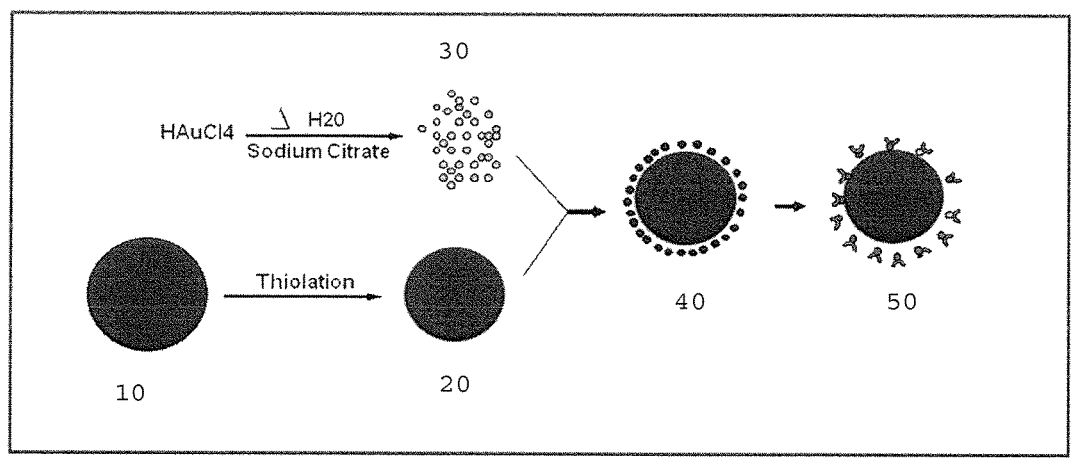
FIG. 1 is a graphical representation showing a flow diagram depicting fabrication of multimodal technology consisting of target-specific ligand adsorbed on to colloidal gold nanoparticles (Au NPs) that covalently attached to poly(epsilon-caprolactone) (PCL) microparticles incorporated with near infrared fluoroscent dye. The targeting ligands used are arginine-glycine-aspartate (RGD) tripeptide to effectively target the alpha-V-beta-III ($\alpha_v\beta_3$) integrin receptor which is over-expressed on pre-cancerous colon epithelial cells, or epidermal growth factor (EGFR) antibody to target pre-cancerous lesions in the oral cavity, respectively. Near infrared dye core consisting of lipophilic DID dye analogues with absoprtion spectrum at 750 nm are used for fluoroscent guided OCT imaging of precancerous lesions.

Disclosed herein are multimodal detection agents and methods of making same. Such agents facilitate more effective early diagnosis of superficial tumor lesions such as in the oral cavity, esophageal, stomach, and colon cancer. Aspects of the detection agents disclosed herein are multimodal detection agents, each comprising a plurality of metallic nanoparticles attached to the surface of a polymeric carrier. Each detection agent further comprises one or more target-specific binding agents attached to the metallic nanoparticles or the polymeric carrier.

The multimodal technology is based, in part, on topical administration of target-specific binding agents to the multimodal detection agents. As used herein, the term "target-specific binding agent" means a molecule or compound that has an affinity for a target molecule or structure and interacts or associates with the target molecule or compound through van der Waals forces, London forces, covalent bonds, ionic bonds, hydrogen bonds or a combination of these interactions.

The compositions disclosed herein can also encapsulate one or more imaging agents. As used herein, the term "encapsulate" means to enclose within or associate with the polymeric carrier. The encapsulation can include association of a molecule or compound at the surface of the polymeric carrier or within the polymeric carrier. Such imaging agents include fluorophores, radiolabels, X-ray contrast, RAMAN spectroscopy agents, and positron emission tomography agents. Examples of fluorophores include rhodamine, fluorescein, isothiocyanate, phycoerythrin, phycocyanin, fluorescamine, and metal chelates. Examples of radiolabels include $^3$H, $^{123}$I, $^{125}$I, $^{131}$I, $^{32}$P, $^{35}$S, $^{14}$C, $^{51}$Cr, $^{36}$Cl, $^{57}$Co, $^{55}$Fe, $^{59}$Fe, $^{90}$Y, $^{99}$mTc (metastable isomer of Technetium 99), and $^{75}$Se. Furthermore, X-ray contrast agents include Diatrizoate (Hypaque 50), Metrizoate (Isopaque 370), Ioxaglate (Hexabrix), Iopamidol (Isovue 370), Iohexol (Omnipaque 350), Ioxilan (Oxilan 350), Iopromide (Ultravist 370), and Iodixanol (Visipaque 320). Other agents include 2,2,6,6-tetramethylpiperidine-1-oxyl (TEMPO) group, DID fluorescent dye analogs, and perdeuterated alkyl or aryl phosphonium groups. Methods of encapsulating imaging agents within a particle are known in the art. For instance, the solvent displacement method has been used to encapsulating nucleic acids, small molecules, and peptides (see, e.g., Oster et al. *Journal of Controlled Release* (2006) 111(3): 371-381; Ribeiro et al. *Food Hydrocolloids* 22(1): 12-17;).

The polymeric carrier can be any structure and composed of a material that allows for encapsulation of an imaging agent and attachment of metallic nanoparticles. In certain embodiments, the polymeric carrier can be constructed of a core particle comprising one or more of silica, poly(epsilon-caprolactone), poly(d,l-lactide-co-glycolide), and/or modifications thereof. The core particle can also be an aggregation of a dye or other imaging agent. Other materials useful for production of a core particle include polymers such as polythiolates, cysteine containing peptides, polyacrylates, polyacrylic acid, polyvinyl pyrrolidone (PVP), polyethylene glycol (PEG), polynucleotides, poly(hydroxyethyloxazoline), polynucleic acid, poly(hydroxyethylmethacylate), polyallylamine, polyaminoacids, polysaccharides, especially chitosan, carbophil, carbomer and carbopol, poly (dimethylaminalkyl methacrylates) and poly(dimethylaminalkyl acrylates) and the copolymers poly (dimethylaminalkyl methacrylates-co-trimethylaminoalkyl methacryalte) and poly(dimethylaminalkyl acrylates-co-trimethylaminoalkyl acrylate). Methods of producing the carrier are known in the art and include the single emulsion method and solvent displacement method (see, e.g., Furtado Mosqueira et al. *Journal of Pharmaceutical Sciences Special Issue: Papers from the* 1999 *Macromolecular Drug Delivery Conference* (2000) 89(5): 614-626; Rosca et al. *Journal of Controlled Release* (2004) 99(2): 271-280).

Certain aspects of the multimodal detection agents include one or more gelatin layers attached or associated with the core particle of the polymeric carrier. As used herein, the term "gelatin" means any hydrophilic substance or material capable of absorbing an aqueous solution and forming a gel. Exemplary gelling materials include gelatin, polysaccharides, cellulose, collagen, keratin, polyketal, and beta-lactoglobulin. In certain embodiments, the gelling materials are biodegradable or biocompatible. Methods of preparing polymeric materials are well known in the art (see, e.g., Papisov M. I. et al. *Biomacromolecules* (2005) 6: 2659-2670; Mathiowitz et al. *Nature*, (1997) 386: 410-414; Tsung et al. *AAPS PharmSci.* (2001) 3(1): Article 11).

The gelatin layer or core particle can be derivatized with a variety of groups, including target-specific binding agents. Derivatization of organic polymers can be performed to expose selected reactive groups at their surface (see, e.g., Townsend, S. A, et al. *Biomaterials* (2007) 28(34): 5176-5184; Weiss, B., et al. *Bioconjugate Chemistry* (2007) 18(4): 1087-1094; and Gindy, M. E., et al. *PMSE Preprints* (2006) 95:989-990). Furthermore, attaching target-specific binding agents, such as proteins, peptides, antibodies, and small molecules, to a polymer is known in the art (see, e.g., U.S. Pat. No. 7,022,336; Bumgarner et al. *J Control Release* (2009) 137(2):90-7; Sy et al. *Biomaterials* (2010) 31(18): 4987-94; Balmayor et al. *J. R. Soc. Interface* (2011) 10.1098/rsif.2010.0531). A target-specific binding agent can be a small molecule that binds a target, ligand, peptide (e.g., arginine-glycine-aspartate ("RGD") tripeptide), protein, antibody, Fab fragment, F(ab')2 fragments, and peptidomimetic compounds. Exemplary targets include receptors (e.g., alpha-V-beta III integrin receptor and EGFR receptor), phospholipids, glycoproteins, and proteins.

In certain aspects, the multimodal detection agents comprise metallic nanoparticles attached to the surface of the polymeric carrier. The surface of the polymeric carrier can be either a core particle as described herein or a gelatin layer attached to the surface of the core particle. A variety of metallic nanoparticles are suitable for use in the compositions. In certain embodiments, suitable nanoparticles are essentially spherical in form. In other embodiments, other forms are used. The nanoparticles are composed of a metal. In specific embodiments, metallic nanoparticles comprise metals and metal oxides of gold, silver, and iron. The metallic nanoparticles can be homeogeneous or blended from two or more metals. The surface of the nanoparticles has one or more chemically reactive groups suitable for functionalization with a target-specific binding agent. In some embodiments, the surface of the nanoparticles contains multiple, evenly distributed reactive groups of a single type. Some non-limiting examples of nanoparticles suitable for use are gold, thiol residues, cross-linked iron, aminopropylsilyl acyl oxide (CLIO) protecting group, silver, amine organic polymer, COOH or $NH_2$ or COOH quantum dots.

The size of the metallic nanoparticles, e.g., the average (mean) diameter, is in the range from about 2 nm to about 100 nm; from about 5 nm to about 50 nm; from about 2 nm to about 30 nm; and from about 10 nm to about 20 nm. The size distribution within a set of nanoparticles is a normal distribution; however, for certain applications a set can have other size distributions, such as bimodal or other types of distribution. Size distribution and average diameter of the nanoparticles can be measured by any method known in the art, including but not limited to light scattering, electron microscopy, and size exclusion chromatography.

In specific embodiments, the multimodal detection agent comprises colloidal gold adsorbed to poly(epsilon-caprolactone) (Au-PCL) or silica microparticles and fluorescence-guided scattering technology. While enhanced-contrast fluorescence imaging helps to better localize suspicious lesions, OCT is used under fluorescence guidance to visualize tissue morphology, and thus to serve as a confirmatory tool for neoplastic disease.

The multimodal detection agents disclosed herein are useful in known imaging techniques. For instance, the multimodal detection agents can be used in optical coherence tomography ("OCT") imaging. Other detection methods include fluorescence microscopy, electron paramagnetic resonance, Raman spectroscopy, and positron emission tomography.

In certain embodiments, the multimodal technology is constructed using PCL or silica microspheres as a core material. The core material further incorporates a near infrared fluorescent dye as showed in FIG. 1. The single emulsion method can be employed to form the core particle encapsulating a dye. In the embodiment shown in FIG. 1, the incorporation is performed in the presence of cetyltriethylammonium bromide. In FIG. 1, the amine-modified PCL particle (i.e., polymeric carrier) with near infrared core particle 10 is constructed according to the single emulsion method. The PCL polymeric carrier 10 is thiolated according to known techniques to form a thiol functionalized polymeric carrier 20. In the embodiment shown in FIG. 1, the cationic PCL microparticle surface are modified with thiolated gelatin to allow covalent attachment of colloidal gold nanoparticles 30 (10 nm-20 nm). The surface of Au-PCL microparticles 40 can be modified with target-specific binding agents such as EGFR specific antibodies 50. In certain embodiments, the target-specific binding agents are arginine-glycine-aspartate (RGD) tripeptides for targeting the alpha-V-beta-III ($\alpha_v\beta_3$) integrin receptor. In the embodiment shown in FIG. 1, DID fluorescent dye analogs with absorption spectrum at 750 nm are used as near infrared dyes for fluorescent guided OCT imaging of pre-cancerous lesions.

The multimodal detection agent, upon topical administration, can bind specifically to particular cells. In certain embodiments, the cells are pre-cancerous and bound through the interaction of RGD and EGFR with the over-expressed receptors on such cancerous cells. When such binding occurs, the fluorescence contrast originating from the PCL core helps to better localize suspicious lesions. Then OCT is used under fluorescence guidance to visualize tissue morphology and thus to serve as an early diagnosis tool for cancer presence.

The compositions disclosed herein can be administered orally, topically, or parenterally (e.g., intranasally, subcutaneously, intramuscularly, intravenously, or intra-arterially) by routine methods in pharmaceutically acceptable inert carrier substances. The compositions can be administered in a dosage of 0.25 µg/kg/day to 5 mg/kg/day and in dosages of 1 µg/kg/day to 500 µg/kg/day. Optimal dosage and modes of administration can readily be determined by conventional protocols.

2. Methods of Fabrication

Aspects disclosed herein include methods of manufacturing a multimodal imaging agent. In particular, the methods comprise fabricating a polymeric core particle. For instance, the core particle can be produce by dissolving a polymer, such as PCL, in a solvent (e.g., dichloromethane) in the presence of an imaging agent. Such mixtures can be subjected to the single emulsion method where the mixture of polymer and imaging agent in the solvent are emulsified with an aqueous phase to produce an oil-in-water (O/W) emulsion. The core particle of the detection agent is allowed to form with the imaging agent encapsulated within the core particle. The imaging agent makes the detection agent visible in detection instruments such as a PET instrument.

Certain aspects of the methods disclosed further comprise adding at least one coating to the polymeric core particle to form a polymeric carrier. Such coatings include gelatin, for example. The surface of the core particle can be modified with thiolated gelatin. For thiolation, a solution of gelatin can be prepared in a thiolation agent (e.g., 2-iminothiolane). The thiol functional groups (SH—) of thiolated gelatin can easily attach to the surface of the amino group of the polymer used to make the core particle of the detection agent.

In certain aspects, the methods further comprise attaching one or more metallic nanoparticles to the multimodal detection agent. This can be accomplished using, for instance, metals that are unreactive in a biological system (e.g., gold, silver, iron oxide) and are milled to produce nanometer-sized particles. Such particles can be obtained from various procedures known in the art (see, e.g., McFarland et al. *J. Chem. Educ.* (2004) 81 (4): 544A; Luna Martinez et al. *Mater. Sci. Forum: Adv. Elec. Microscop. Nanomat.* (2010) 644: 51-55; Gardea-Torresday et al. *Journal of Nanoparticle Research* (1999) 1(3): 397-404; Zhou et al. *Chem. Mater.* (1999) 11 (9): 2310-2312). Nanoparticles can also be obtained commercially from Sigma-Aldrich (St. Louis, Mo.) and Nanostructured & Amorphous Materials, Inc. (Houston, Tex.). The multimodal detection agent can be covered with metallic nanoparticles using known procedures, such as coating gold nanoparticles by reduction of tetrachloroauric acid with sodium citrate, which leads to the formation of 20-30-nm gold particles attached to the surface of the multimodal detection agent. For gold nanoparticles of 2 nm to 10 nm, sodium borohydride is used. In certain embodiments, metallic nanoparticles can be used to facilitate target-specific binding agent attachment, which will enhance imaging contrast by intensively reflecting the light. The nanoparticles' surface can be functionalized with the target-specific binding agent, such as with a linear peptide sequence (e.g., ACD/CRG/DCF/CGG/GGG/COOH), which can be synthesized using known methodologies.

3. Kits

One or more of the components needed for preparing the multimodal detection agents can be conveniently provided in the form of a kit. A kit can include instructions for use of the components to prepare functionalized multimodal detection agents according to the disclosed methods, as well as one or more reagents useful in carrying out any of the coupling, blocking, or unblocking reactions. A kit can also include packaging materials.

The disclosure is further illustrated by the following examples. The examples are provided for illustrative purposes only. They are not to be construed as limiting the scope or content of the disclosure in any way.

EXAMPLES

Example 1

A Nanotechnology-Based Multimodal Approach for More Effective Diagnosis of Early Stage Colon Cancers Near-infrared fluorescent dye labeled PCL microparticles with an average size of 1.5 μm were fabricated by the single emulsion process and surface coated with 20 nm colloidal gold by adsorption on to thiol-modified gelatin coating. These particles were then functionalized with an arginine-glycine-aspartate (RGD) tripeptide having a cysteine group to attach to the gold surface using thiol-gold covalent bond to effectively target the alpha-V-beta-III ($\alpha_v\beta_3$) integrin receptor, which is over-expressed on pre-cancerous epithelial cells. Preliminary testing of functionalization efficacy was performed on HT29 and SW480 colon cancer cell lines from American Type Culture Collection (ATCC, Richmond, Va.) (Sainsbury, et al. (2007) *J. Phys. Chem. C*, 111: 12992-12999). The following is a brief description of the methodologies used.

Highly engineered Au-PCL microspheres were fabricated to be used as a contrast agent. Gold nanoparticles, 20 nm in size, were used to facilitate RGD attachment and enhance OCT imaging contrast by intensively reflecting the light. The nanoparticles' surface was functionalized with RGD with a linear sequence—ACD/CRG/DCF/CGG/GGG/COOH—which was synthesized at the research core facility at Tufts University (MA, USA). This peptide specifically recognizes the anb3-integrin receptor, which is overexpressed by the precancerous epithelial cells. Although other sequences were tested as well, this sequence showed the highest affinity to four cancer cell lines used in recent studies: human colon adenocarcinoma grade II-HT 29, human colon adenocarcinoma SW480, human cervical cancer HeLa, and human esophageal cancer HET1A. A NIR fluorescent dye (D-12731 [Invitrogen, USA], also known as DiR), was used to label these microparticles and make them visible in the fluorescence channel of the instrument.

Briefly, 1 g of PCL was dissolved in 16.7 ml of dichloromethane ($CH_2Cl_2$), and then the DiR dye (10-μM concentration) was added. The resulting oil-phase mixture was emulsified with the aqueous phase of 1 g cetyltrimethylammonium bromide (CTAB) in 333 ml of deionized water (resistivity: 18.2 M W; Millipore Corp., USA) using Silverson homogenizer (Silverstone Machines Ltd, CA, USA) at 8000 rpm and at room temperature for 5 min to produce an oilin-water (O/W) emulsion. The emulsion was then stirred at room temperature for 24 h to allow the evaporation of dichloromethane and the formation (solidification) of the PCL microparticles. The resulting microparticles suspension was centrifuged at 4000 rpm for 10 min, the pellet was washed two to three times with water to remove excess CTAB, and then freeze dried. The microparticles were then covered with gold nanoparticles, which were fabricated using a standard procedure by the reduction of tetrachloroauric acid with sodium citrate, which leads to the formation of 20-30-nm gold particles.

To attach citrate gold nanoparticles, the surface of PCL particles was first modified with thiolated gelatin. For thiolation, a solution of gelatin was prepared and incubated with 2-iminothiolane, a cyclic thioimidate compound that is stable at both acidic and neutral pH. In total, 1 g of gelatin was dissolved in 100 ml of distilled water, and then incubated with varying masses of 2-iminothiolane (10-100 mg/g of gelatin) at room temperature for 15 h. Any unreacted iminothiolane was removed by repeated dialysis against 5 mM hydrochloric acid, followed by 1 mM hydrochloric acid solution for 24 h each, with repeated water changes in a 2-1 beaker. The purified thiolated gelatin was freeze-dried for further use, and stored at 4° C. The thiol functional groups (SH—) of thiolated gelatin can easily attach to the surface of the amino group of CTAB over PCL microparticles. To accomplish this, 1 g of PCL-CTAB microparticles were dispersed in 350 ml of purified water, and 100 mg of thiolated gelatin in 20 ml of 10 mM ethylenediaminetetraacetic acid (EDTA) solution was added. Then, the reaction mixture was stirred vigorously for 1 day at 4° C. Excess thiolated gelatin was removed from the thio-functionalized PCL particles by centrifugation at 4000 rpm for 10 min.

After washing twice with water, the pellet was redispersed in 150 ml of water. The 5% wet weight of gold nanoparticles was added slowly (2-3 h) dropwise into the rapidly stirring thio-functionalized PCL particles, which were then transferred to 4° C. for overnight mild stirring. After this, the sample was centrifuged, and the pellet was redispersed in water and freeze-dried.

Figure 2:
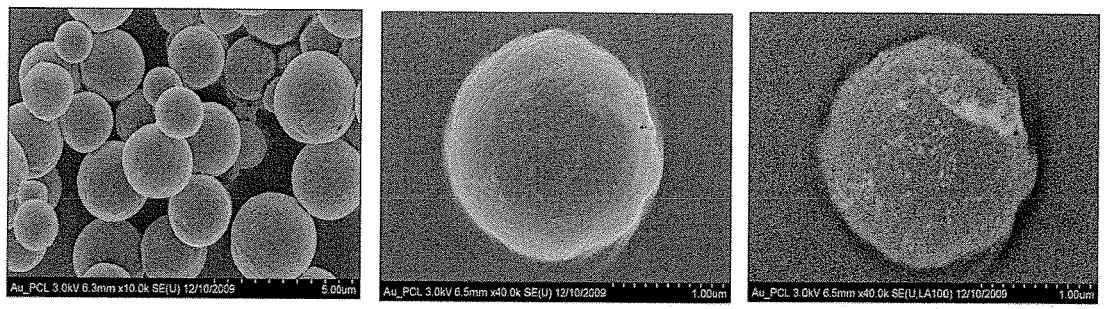
FIG. 2 is a pictorial representation showing a scanning electron micrographs of Au nanoparticle coated PCL microparticles with near infrared dye core. The microparticles approximate size is 1.6 µm in diameter. Coverage of the PCL microparticle surface with Au NPs is shown in the magnified image (centre) and back scattered image (right).

The RGD peptide was then attached to microparticles. The RGD (0.1 nM) was diluted with 2 ml of distilled water. A total of 200 mg of well-characterized Au-PCL nanoparticles were dispersed in 50 ml of deionized water. This dispersion was split into two conical flasks containing 100 ml of the dispersed Au-PCL nanoparticle particles. Both conical flasks were wrapped with aluminum foils to prevent light exposure. In one of the conical flasks, 1.5 ml of RGD was added and stirred for 48 h at 4° C. (in the dark). In the other flask, under the same conditions, 1.5 ml of RGD was added, and then 20 mg of Trout's reagent was added and stirred for 48 h at 4° C. Subsequently, the reaction mixture was centrifuged to collect the RGD-bound nanoparticles, and washed twice with distilled water and centrifuged. Then, 5 ml of water was added to the microparticles and lyophilized to obtain the purified particles. After fabrication, the gold nanoparticle coated PCL microparticles were characterized for size and size distribution using a Multisizer™ 3 (Beckman Coulter, CA, USA). This instrument measures the change in the electrical resistance produced by nonconductive particle in the electrolyte solution. The microparticles were diluted with water, and the diluted suspension was added to the glass beaker containing the standard electrolyte solution until a suitable concentration was obtained for particle-size measurement. All measurements were carried out at room temperature. An average size of 1.6 μm with a standard deviation of 0.5 μm was observed. A scanning electron microscopy image of the microparticles is shown in FIG. 2 Hitachi S-4800 (Hitachi High-Technologies, UK) field emission scanning microscope at an acceleration voltage of 20 kV was used. The gold-coated surface morphology of the freeze-dried microparticles was observed in the reflectance mode. A custom-built inverted microscope with a fluorescence channel was used for the preliminary testing of the imaging contrast agent on cell cultures and, at a later duration in the study, on thin samples of tissue (50 μm in thickness). The inverted microscope platform was constructed by modifying a Leitz Laborlux upright microscope (Leitz, Germany). A Xenon arc lamp provided a continuous wide band of light, which was used as an illumination source for the fluorescence excitation, and a halogen lamp was used as an illumination source for brightfield imaging. A light-guide fiber bundle and relay optics were used to deliver the excitation beam from the Xenon lamp to a Nikon objective lens (100× oil immersion; 1.25 numerical aperture [NA]). The fluorescence signal from the sample was collected by the same objective lens and relayed to a charge-coupled device (CCD) camera (Rolera XR; Q-Imaging, BC, Canada). In the fluorescence mode, a NIR filter (Model 41037; Chroma, VT, USA) was placed in front of the CCD camera to reject the back reflection signal from the sample, and to allow only the emission from the fluorescence dye to reach the CCD sensor. In bright-field imaging, a condenser lens was used to send the illumination beam from a halogen source to the sample. The image was magnified by the same objective lens, and relayed to the CCD sensor.

An existing OCT imaging system based on the spectral domain (SD) approach, previously built at Physical Sciences (MA, USA) was used for OCT imaging. A fluorescence channel was added to the instrument's probe.

The data acquisition software was upgraded to allow for simultaneous OCT—fluorescence imaging. The SD-OCT/fluorescence imaging system consists of five subsystems: light sources (835 and 1310 nm), fiberoptic interferometer (2×2 fiber splitter, circulator, and reference and sample arm optics), spectral detection unit (diffraction grating, spectrometer lens system and digital InGaAs camera), imaging probe, and data acquisition and processing unit (computer, camera board and display). The imaging probe has two channels, allowing for both OCT and fluorescence imaging. This probe has an excitation port that uses a 745-nm laser diode (Model QFLD 745; QPhotonics, MI, USA) to excite the NIR dye, and an OCT imaging port. The OCT channel consists of a beam collimator, two scanning mirrors that generate an OCT raster and a 5× scanning lens (Model LSM03; Thorlabs, NJ, USA).

A custom dichroic filter (Andover Corporation, MA, USA) is used to combine the OCT and fluorescence excitation beams on the sample, and simultaneously collect both OCT and fluorescence images. A NIR-enhanced response camera (Rolera XR) is used for fluorescence imaging. The excitation light is blocked by a NIR filter (Model 41037, Chroma Technology Corp., VT, USA). The bench-top imaging probe can collect raster OCT images (maximum 7×7 mm) with an axial resolution of approximately 10 μm in tissue, and relatively large-field fluorescence images (25×25 mm) at relatively high frame rates (20 frames/s or higher, depending of the image resolution).

Testing of the multimodal detection agents produced above was performed on a HT29 colon cancer xenograft model in nu/nu nude mice. Mice were inoculated with the cells under the left flank and the tumor mass was allowed to grow for about 10 days. Following sacrifice, the tumor was harvested and treated with control (unmodified) and RGD-modified Au-PCL microparticles. Tumor and normal tissue sections were cut to 20 μm thickness on 10 slides for tumor sample and 10 slides for normal tissue sample. The tissue samples were kept in Tissue Embedding Media (TEM), and washed with PBS to get rid of the embedding media, 50 mg of DIR-PCL Au particles (freeze dried) were used as control particles (un-modified). They were dispersed in PBS to 2 mg/ml. If there was aggregation, stirring at 4° C. for 30 min was performed. 50 mg of RGD modified DIR-PCL-Au particle suspension was made by adding 2 mg of pure RGD to 50 mg of DIR-PCL-Au particles in 25 ml of water. This sample was centrifuged at 4000 g for 10 min and the pellet dispersed in PBS to 2 mg/ml. Tissue slices were then obtained and imaged using OCT and fluorescence microscopy.

Strong binding of the RGD-functionalized microparticles and weak binding of the unfunctionalized microparticles was observed in HT29 and SW480 colon cell lines. Both the OCT and fluorescence images taken before and after incubation on both normal and tumor tissue samples showed increased contrast (enhanced scattering and fluorescence contrast, respectively) on the tumor tissue samples.

These results show that topical administration of RGD-functionalized microparticles in combination with fluorescence-guided OCT imaging helps to more effectively localize early stage colon cancers.

Example 2

Development of EGFR-Targeted Gold Nanoparticle-Coated Poly (Epsilon-Caprolactone) Microparticles for Detection of Oral Pre-Cancer Lesions Current oral cancer diagnosis is based on tissue transformation, which is confirmed by biopsy and pathological analysis. Early detection technology specifically for pre-cancerous lesions that can be used in routine dental exam provides a favorable clinical outcome.

The main objective of this example was to develop epidermal growth factor receptor (EGFR)-targeted gold nanoparticle-coated poly(epsilon-caprolactone) (Au-PCL) microspheres as a dual-detection technology pre-cancerous lesions in the oral cavity.

Fluorescent dye-encapsulated PCL microparticles (2 mm-3 mm in diameter) were formed using the single emulsion method where the polymer in organic solvent is mixed with an aqueous solution of cetyltriethylammonium bromide and emulsified under controlled stirring. The resulting microparticle size and surface morphology is dictated by the polymer concentration, ratio of organic to aqueous phases, rate of addition, and the stirring speed. These parameters were optimized to generate PCL microspheres of 1 μm-5 μm in diameter and having a positively-charged surface. The positively-charged (cationic) microsphere surfaces were modified with thiolated gelatin to allow for covalent attachment of gold nanoparticles (20 nm-40 nm) through the thiol-gold linkage. The surfaces of Au-PCL microspheres were then modified with EGFR antibody by adsorption from an aqueous solution. The formulations were characterized for size, surface charge, and morphology. Cell binding studies were performed to confirm EGFR-specific interactions using differential interference contrast (DIC), confocal reflectance, and 2-photon fluorescence microscopy.

The results show that cationic PCL microparticles could successfully encapsulate hydrophobic fluorescent dye and could be functionalized with gold nanoparticles and EGFR-specific antibody. The EGFR-targeted microparticles also showed very efficient binding to EGFR over-expressing cancer cell lines, including HCPC-1 relative to unmodified microparticles. EGFR-specific binding could be displaced by an excess of the soluble antibody.

Figure 3:
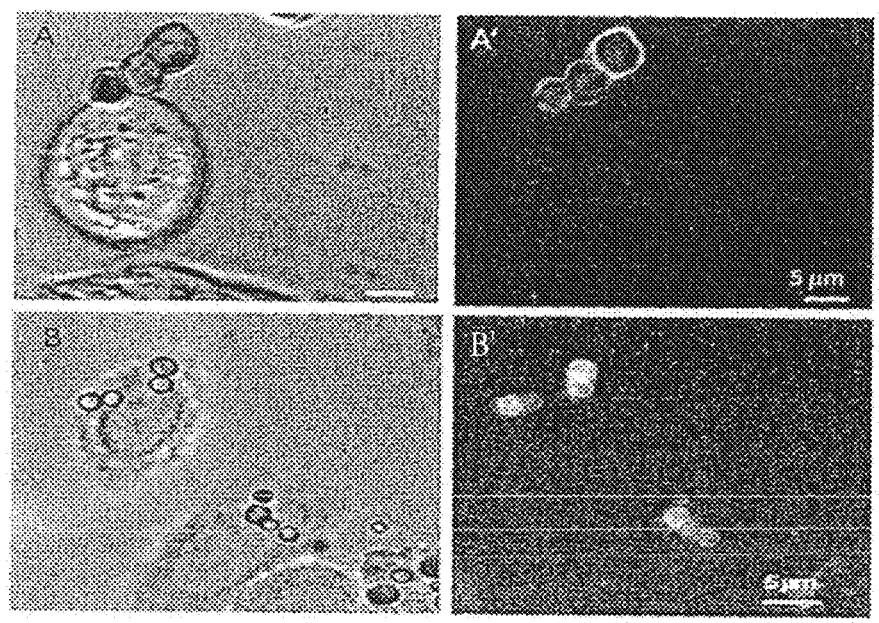
FIG. 3 is a pictorial representation showing an in vitro study of binding efficiency of RGD-functionalized Au-PCL-DiR microparticles in HT29 (A, A') and SW480 (B, B') colon cancer cells which over express $\alpha_v\beta_3$ integrin receptors. Bright field (left) and fluorescence (right) images were taken with 100× oil immersed Olympus objective.
Figure 4:
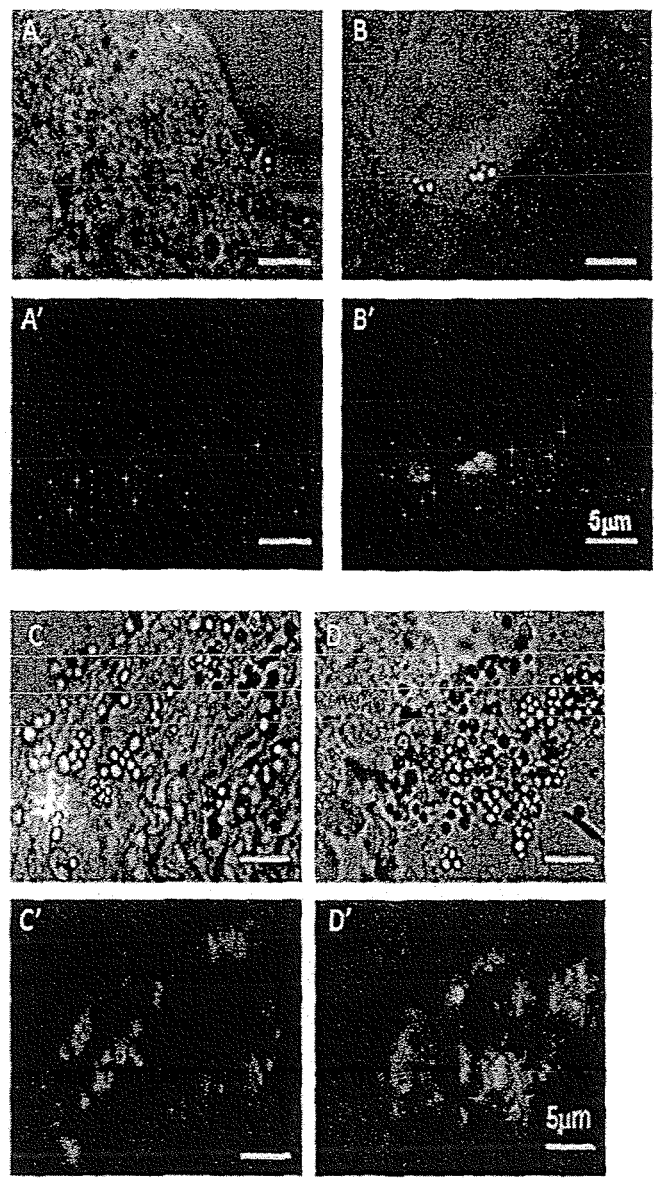
FIG. 4 is a pictorial representation showing an ex vivo study showing binding efficiency of RGD-functionalized Au-PCL-DiR microparticles in normal and HT 29 tumor tissues obtained from the subcutaneous xenograft model in nu/nu mice. A, B—bright field images of the normal fibrous and adipose tissue; A', B'—corresponding fluorescence images; C,D—bright field images of the tumor tissue; C', D'—corresponding fluorescence images. Images were taken with a 100× oil immersed Olympus objective.

EGFR-targeted Au-PCL microspheres offer a useful platform for reflectance and fluorescence imaging in detection of EGFR over-expressing oral pre-cancerous lesions. In vitro and ex vivo data (FIGS. 3 and 4) shows that this multimodal technology could efficiently bind to pre-cancerous cells that over-express the ligand specific receptors, produce enhanced fluorescence contrast to localize the affected area and subsequent OCT imaging to confirm the cancer presence.

All publications, patent applications, patents, and other references mentioned herein are incorporated by reference in their entirety. In case of conflict, the present specification, including definitions, will control. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

The invention claimed is:

1. A multimodal imaging agent comprising a plurality of metallic nanoparticles attached to a surface of a polymeric carrier, wherein the polymeric carrier comprises a polymeric core particle and at least one layer of gelatin having exposed thiol groups, wherein the polymeric core particle encapsulates a near infrared fluorescence dye and the metallic nanoparticles are attached to the exposed thiol groups, and wherein the detection agent further comprises one or more target-specific binding agents attached to the metallic nanoparticles or the polymeric carrier.

2. The multimodal imaging agent of claim 1, wherein the metallic nanoparticles comprise one or more of the metals and metal oxides selected from the group consisting of gold, silver, cobalt, manganese, and iron.

3. The multimodal imaging agent of claim 2, wherein the metallic nanoparticles comprise gold.

4. The multimodal imaging agent of claim 1, wherein the polymeric core particle comprises poly(epsilon-caprolactone), poly(d,l-lactide-co-glycolide), or modified poly(epsilon-caprolactone).

5. The multimodal imaging agent of claim 1, wherein the one or more target-specific binding agents is an antibody, Fab fragment, or binding fragment thereof, a peptide sequence that specifically targets cell surface receptors, a peptide sequence that specifically targets epidermal growth factor receptor (EGFR), an arginine-glycine-aspartate tripeptide, or binds to alpha-V-beta III integrin receptor.

6. The multimodal imaging agent of claim 5, wherein the one or more target-specific binding agents is an EGFR-specific antibody.

7. The multimodal imaging agent of claim 2, wherein the metallic nanoparticles are about 2 nanometers to about 30 nanometers.

8. The multimodal imaging agent of claim 1, wherein the polymeric carrier is about 500 nanometers to about 10 microns.

9. The multimodal imaging agent of claim 7, wherein the metallic nanoparticles are about 10 nanometers to about 20 nanometers.

10. The multimodal imaging agent of claim 8, wherein the polymeric carrier is about 1.5 microns.

11. The multimodal imaging agent of claim 1, wherein the target-specific binding agent is attached to the metallic nanoparticle.

12. The multimodal imaging agent of claim 1, wherein the target-specific binding agent is attached to the metallic nanoparticle and the polymeric carrier.

13. A method of manufacturing the multimodal imaging agent of claim 1, the method comprising:
    (a) fabricating a polymeric core particle, wherein the particle encapsulates a near-infrared fluorescence dye;
    (b) adding at least one coating comprising thiol-modified gelatin to the polymeric core particle to form a polymeric carrier;
    (c) attaching one or more metallic nanoparticles to the thiol groups of the coating; and
    (d) functionalizing the at least one coating or one or more metallic nanoparticles with a target-specific binding agent.

14. The method of claim 13, wherein the polymeric core particle comprises poly(epsilon-caprolactone).

15. The method of claim 13, wherein the one or more metallic nanoparticles comprises one or more of the metals and metal oxides selected from the group consisting of gold, silver, and iron.

16. The method of claim 13, wherein the metallic nanoparticles are about 2 nanometers to about 30 nanometers.

17. The method of claim 13, wherein the polymeric carrier is about 500 nanometers to about 10 microns.

18. The method of claim 13, wherein the target-specific binding agent is an EGFR-specific antibody, an arginine-glycine-aspartate tripeptide, or binds to alpha-V-beta III integrin receptor.

19. The method of claim 13, wherein the polymeric carrier is about 1.5 microns.

20. The method of claim 13, wherein the metallic nanoparticles are about 10 nanometers to about 20 nanometers.

21. The method of claim 13, wherein the target-specific binding agent is an antibody, Fab fragment, or binding fragment thereof.

\* \* \* \* \*